United States Patent
Field

(10) Patent No.: US 8,052,658 B2
(45) Date of Patent: Nov. 8, 2011

(54) DRUG-ELUTING TISSUE MARKER

(75) Inventor: Steven E. Field, Grand Rapids, MI (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 832 days.

(21) Appl. No.: 11/538,918

(22) Filed: Oct. 5, 2006

(65) Prior Publication Data

US 2007/0087026 A1    Apr. 19, 2007

Related U.S. Application Data

(60) Provisional application No. 60/596,636, filed on Oct. 7, 2005.

(51) Int. Cl.
*A61M 25/00* (2006.01)

(52) U.S. Cl. .......... 604/264; 600/426; 600/427; 600/431

(58) Field of Classification Search .................. 604/264; 600/3, 426, 427, 431
See application file for complete search history.

(56) References Cited

U.S. PATENT DOCUMENTS

| | | |
|---|---|---|
| 4,401,124 A | 8/1983 | Guess et al. |
| 4,582,061 A | 4/1986 | Fry |
| 5,141,748 A | 8/1992 | Rizzo |
| 5,490,521 A | 2/1996 | Davis et al. |
| 6,056,700 A | 5/2000 | Burney et al. |
| 6,096,070 A | 8/2000 | Ragheb et al. |
| 6,120,536 A | 9/2000 | Ding et al. |
| 6,228,055 B1 | 5/2001 | Foerster et al. |
| 6,261,243 B1 | 7/2001 | Burney et al. |
| 6,335,029 B1 | 1/2002 | Kamath et al. |
| 6,340,367 B1 | 1/2002 | Stinson et al. |
| 6,350,244 B1 * | 2/2002 | Fisher ........................... 600/562 |
| 6,371,904 B1 * | 4/2002 | Sirimanne et al. ................. 600/3 |
| 6,575,991 B1 * | 6/2003 | Chesbrough et al. ......... 606/185 |
| 6,716,444 B1 | 4/2004 | Castro et al. |
| 6,746,773 B2 | 6/2004 | Llanos et al. |
| 6,774,278 B1 | 8/2004 | Ragheb et al. |
| 6,863,685 B2 | 3/2005 | Davila et al. |
| 6,899,731 B2 | 5/2005 | Li et al. |
| 6,918,927 B2 | 7/2005 | Bates et al. |
| 2002/0016625 A1 | 2/2002 | Falotico et al. |
| 2002/0082682 A1 | 6/2002 | Barclay et al. |
| 2002/0098278 A1 | 7/2002 | Bates et al. |
| 2002/0165608 A1 | 11/2002 | Llanos et al. |
| 2002/0193867 A1 | 12/2002 | Gladdish, Jr. et al. |
| 2004/0073284 A1 | 4/2004 | Bates et al. |
| 2004/0210208 A1 | 10/2004 | Paul et al. |
| 2005/0100580 A1 | 5/2005 | Osborne et al. |

FOREIGN PATENT DOCUMENTS

| | | |
|---|---|---|
| EP | 0747069 A2 | 11/1996 |
| EP | 1364628 A1 | 11/2003 |
| FR | 2646674 | 11/1990 |
| WO | 0023124 | 4/2000 |
| WO | 03000308 A1 | 1/2003 |

* cited by examiner

*Primary Examiner* — Kevin C Sirmons
*Assistant Examiner* — Deanna K Hall

(57) ABSTRACT

A drug-eluting tissue marker for marking a site in a tissue mass comprises a drug-eluting portion having a drug for timed release to the site and a material that can be imaged using an imaging technique.

29 Claims, 6 Drawing Sheets

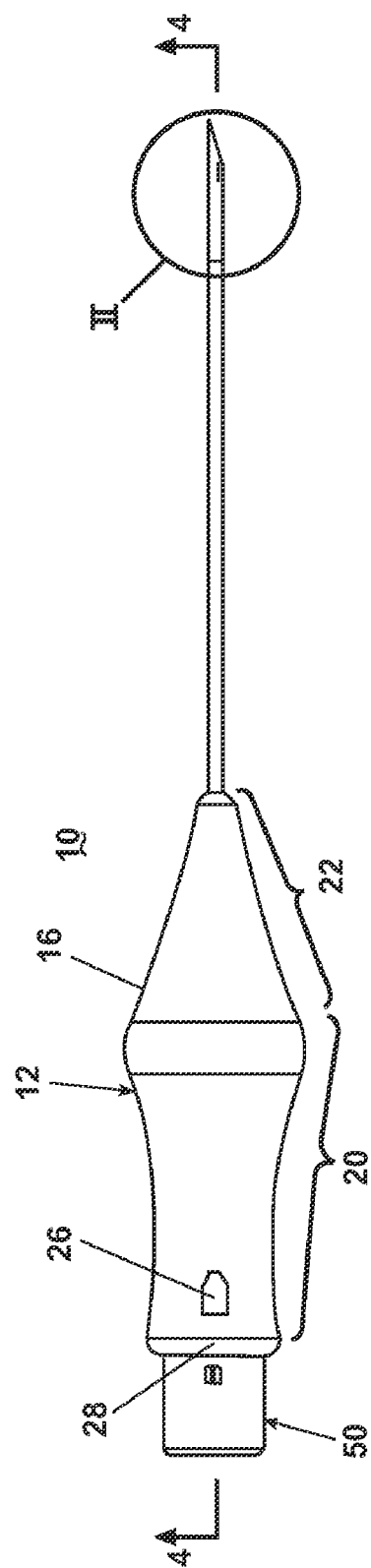
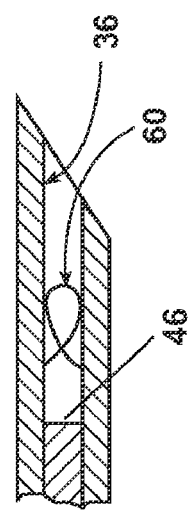
Fig. 1
Fig. 2

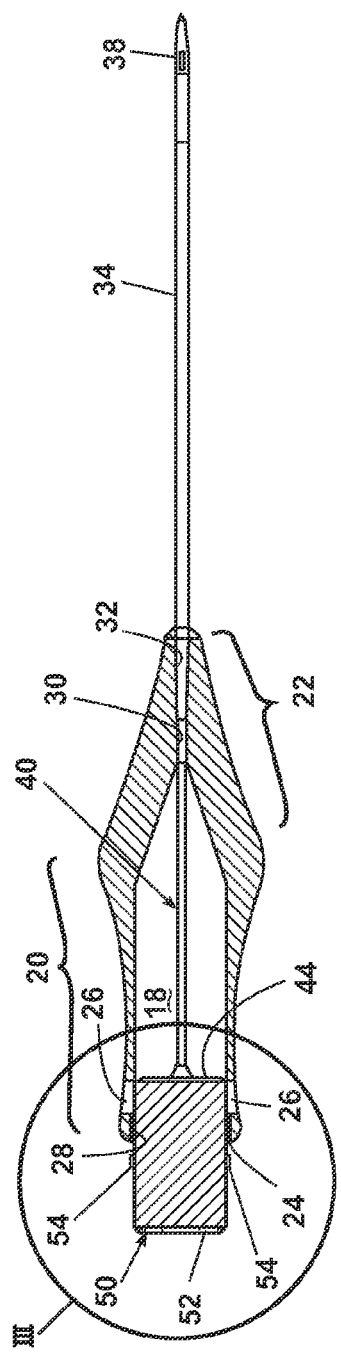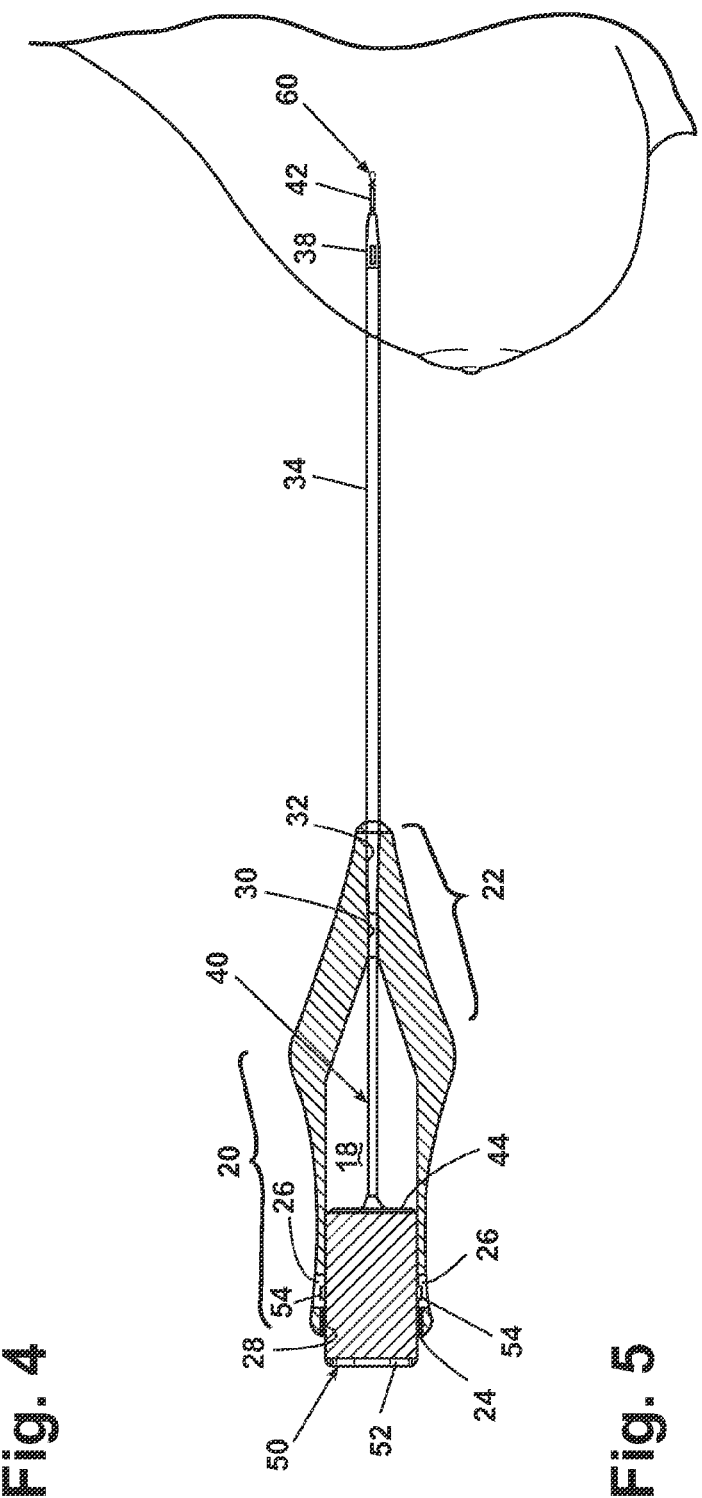

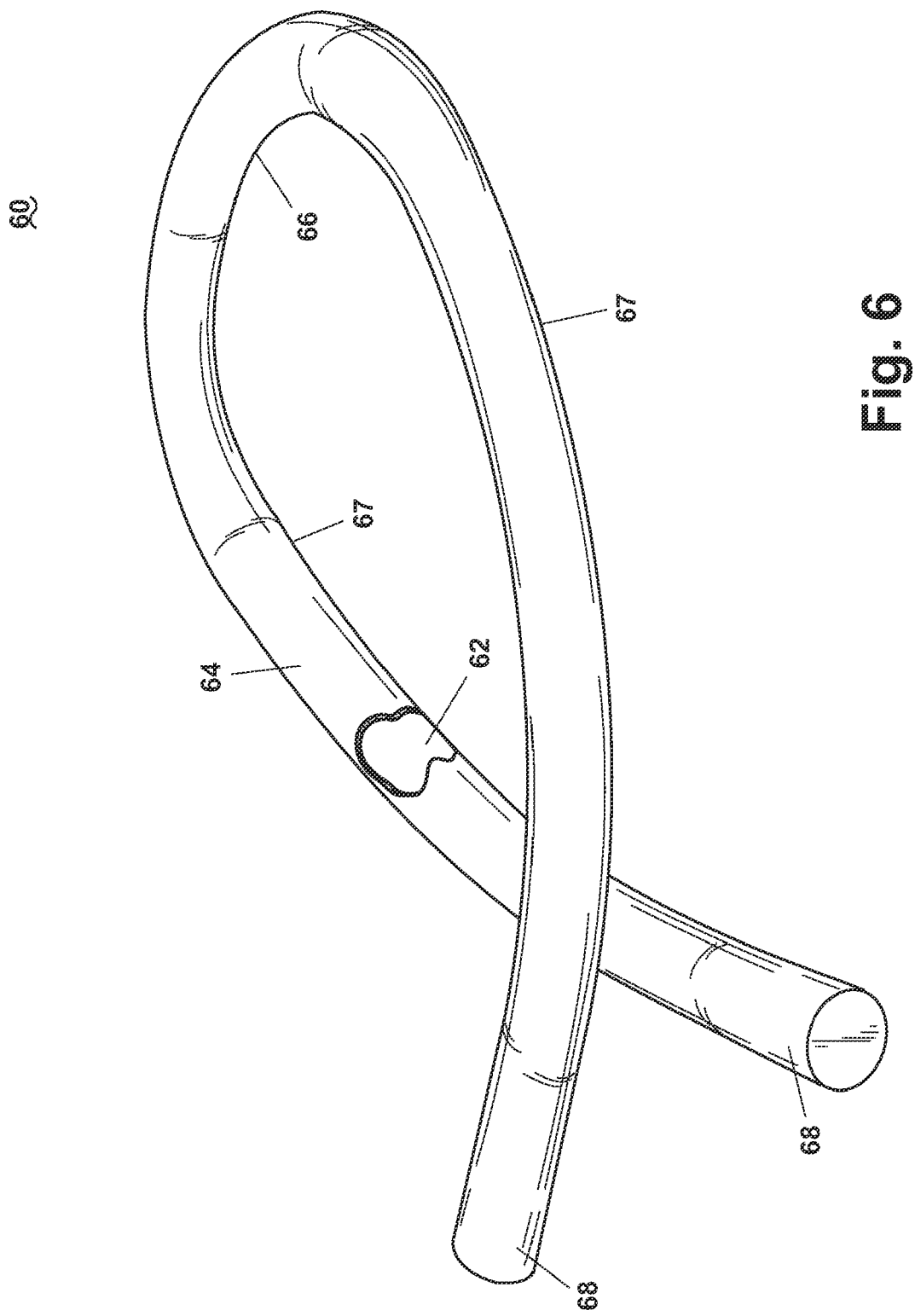

DRUG-ELUTING TISSUE MARKER

CROSS-REFERENCE TO RELATED APPLICATION

This application claims the benefit of U.S. Provisional Patent Application No. 60/596,636, filed Oct. 7, 2005, which is incorporated herein by reference in its entirety.

BACKGROUND OF THE INVENTION

1. Field of the Invention

This invention relates generally to a marker for identifying a site in a tissue mass and particularly to a marker that can elute a drug. In another aspect, the invention relates to a method for introducing a drug-eluting marker into a tissue mass.

2. Description of the Related Art

Tissue markers are implanted in tissue at a site of interest. The markers tend to be very small and biocompatible. They are most commonly implanted after a biopsy is performed to mark the location in case a further procedure at the site is needed. The markers are made of a material that can be imaged using an imaging technique such as magnetic resonance imaging, ultrasonography, or mammography.

Tissue at the site of implantation can be susceptible to related medical conditions such as infection or rejection of the marker, for example, because of the exposure of the tissue during the implantation procedure. There can also be damage to the tissue leading to and at the implantation site. The related medical conditions and tissue damage can require a separate treatment in addition to the implantation of the marker. Some treatments require additional puncturing of the tissue to reach the implantation site for the application of drugs to address the condition or damage.

It is desirable to minimize the need to repuncture the tissue to treat a condition or damage at the implantation site.

SUMMARY OF THE INVENTION

According to the present invention, a tissue marker comprises a marker portion configured to mark a site within a tissue mass, a drug-eluting portion comprising a drug, and a body formed at least in part by the marker portion and the drug eluting portion and configured for implantation into the tissue mass.

The body can have a maximum dimension of 10 mm. The site can comprise a lesion and the body can be configured to mark a lesion having an effective size of at least 2 mm.

At least one of the marker portion and the drug eluting portion can be imageable. The marker portion can be imageable.

The marker can comprises a structure that resists migration of the marker from the site. The structure can be an anchor.

The marker portion can comprise a substrate and the drug-eluting portion can comprise a coating on the substrate.

The drug-eluting portion can be embedded in the marker portion. The marker portion can be bioabsorbable. The marker portion is configured to dissolve within the tissue mass at a predetermined rate and release the drug in a timed release fashion.

The marker portion can at least partially encapsulate the drug-eluting portion. The marker portion can comprise at least one opening that allows the drug to pass out of the marker portion. The marker portion can comprise a spring.

The body can comprise pores and the drug can be contained within the pores to form the drug-eluting portion.

The site can be one of a lesion and a biopsy site.

The drug can be one of an anti-inflammatory, antiplatelet, anticoagulant, antifebrin, antithrombin, cytostatic, antiproliferative, antibiotic, antimicrobial, antioxidant, antiallergic, antitumor, chemotherapeutic, antineoplastic, antimitotic, thrombolytic, fibrinolytic, vasodilator, antiviral, antihypertensive, antisecretory, immunosuppressive, growth factor, growth factor antagonist; antipolymerase, photodynamic therapy, antibody targeted therapy, prodrug, sex hormone, free radical scavengers, radiotherapeutic, radiopaque, radiolabelled, peptides, proteins, and enzyme substance, and any combination thereof.

According to another aspect of the invention, an imaging marker comprises a marker portion and a drug-eluting portion comprising a drug, with at least one of the marker portion and the drug-eluting portion being imageable.

The marker portion can comprise an imageable substrate and the drug-eluting portion can comprise a coating containing the drug applied to the substrate.

The marker portion can comprise a substrate of bioabsorbable material containing the drug.

The marker portion can comprise a substrate that at least partially encapsulates the drug.

According to yet another aspect of the invention, a method for marking a site within a tissue mass comprises placing a marker into the tissue mass and eluting a drug from the marker.

The placing step can comprise placing the marker at a lesion within the tissue mass. The placing step can comprise placing the marker at the site of a biopsy within the tissue mass.

The method can further comprise locating the marker after the placing step. The locating step can comprise one of palpating the tissue mass and imaging the tissue mass. The method can further comprise conducting a medical procedure at the site after the locating step. The method can further comprise locating the site using an imaging system prior to the placing step. The placing step can comprise using an imaging system to embed the marker in a tissue mass.

BRIEF DESCRIPTION OF THE DRAWINGS

In the drawings:

FIG. 1 is a plan view of an introducer used to place a drug-eluting tissue marker at a location in a tissue mass in accordance with the invention;

FIG. 2 is an enlarged sectional view of area II of FIG. 1 illustrating the position of a drug-eluting marker within the introducer prior to ejection;

FIG. 4 is a sectional view taken along line 4-4 of FIG. 1 and illustrating the introducer in a ready condition;

FIG. 5 is a sectional view taken along line 4-4 of FIG. 1 and illustrating the introducer in a discharged condition;

FIG. 6 is a partially broken away perspective view, greatly enlarged, of a first embodiment of the drug-eluting marker according to the invention;

DESCRIPTION OF THE PREFERRED EMBODIMENT

Figure 3:
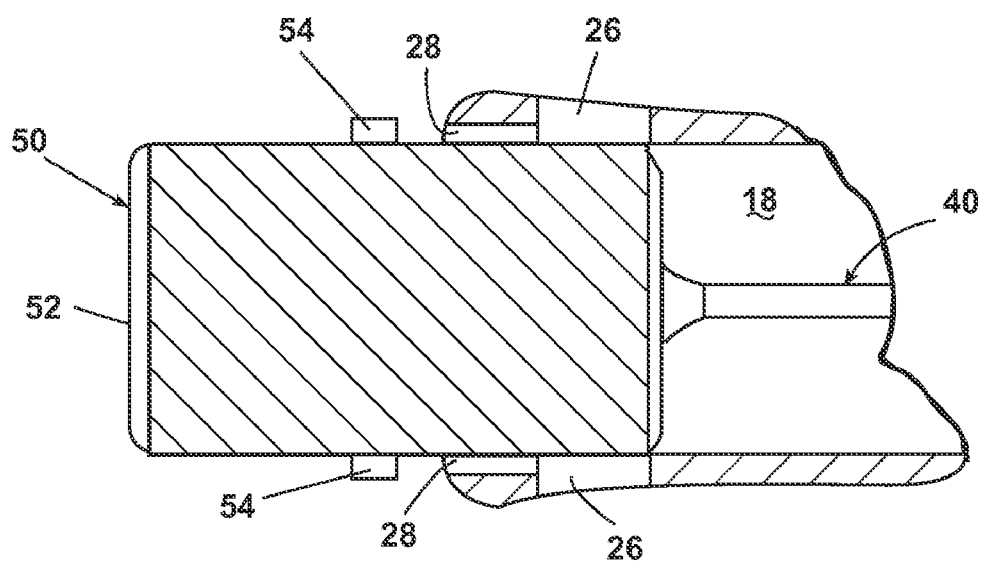
FIG. 3 is an assembly view of area III of FIG. 4 illustrating the arrangement of a handle, a plunger, a cannula, and a stylet of the introducer.

FIGS. 1-4 illustrate a marking apparatus 10 according to the invention, which is capable of the percutaneous placement of a drug-eluting tissue marker 60 at a site within a tissue mass according to the invention. Exemplary tissue masses include breast tissue, skin tissue, muscle tissue, the tissue of glands, such as the prostate, and the tissue of organs such as the lungs, kidney, and liver. For purposes of this application, these types of tissue masses are referred to as soft tissue, which expressly excludes vascular structures.

In the following example, the marking apparatus 10 can be used to place a marker 60 at the location of a tissue biopsy or a lesion. The marking apparatus 10 comprises an introducer 12 and a drug-eluting marker 60 (FIG. 2) contained within the introducer 12. The drug-eluting marker 60 marks a site in a tissue mass. It preferably does not perform a prosthetic function, such as structurally or functionally replacing a part of the tissue mass.

The introducer 12 includes a handle 16 having a hollow interior 18. The handle 16 comprises a grip portion 20 from which extends a tapered nose portion 22. The grip portion 20 defines a rear opening 24 that provides access to the hollow interior 18. A pair of detents 26 are formed in the grip portion 20 near the rear opening 24. Channels 28 are formed on the interior surface of the grip portion 20 and extend from the rear opening 24 to the detents 26.

The nose portion 22 comprises a guide passage 30 extending from the tip of the nose portion 22 to the hollow interior 18 of the handle 16. The guide passage 30 decreases in diameter inwardly from the tip of the nose portion to form a cannula seat 32. Alternatively, the diameter of the guide passage 30 may be substantially equal to or slightly smaller than the outer diameter of a cannula 34, which in any case is press-fit within the cannula seat 32. As is customary, the cannula is formed with a hollow interior 36 and a sharpened tip 38.

A stylet 40 comprising a shaft 42 and a base 44 is received within the hollow interior 18 of the handle 16 in a manner such that the shaft 42 extends through the guide passage 30 and into the cannula interior 36 and the stylet base lies within the hollow interior 18.

A plunger 50 comprises a cylindrical body 52 from which extends a pair of catches 54 at diametrically opposed positions. The cylindrical body 52 is preferably sized so that it is slidably received within the rear opening 24 of the handle 16 where it is so oriented with respect to the handle that the catches 54 are aligned with the guide channels 28.

It should be noted that the marking apparatus 10 is just one example of an apparatus for implanting the marker 60. Many other delivery systems and devices can also be used to implant the drug-eluting marker 60. For example the marker 60 can be implanted in the tissue through a flexible sheath introduced through a vacuum assisted biopsy (VAB) device.

In operation, the introducer 12 begins in the ready condition shown in FIG. 4. In this condition, the stylet shaft is received within the cannula but does not extend to the cannula tip 38 thereby forming a marker recess 46 within the cannula 34, the drug-eluting marker 60 is disposed within the marker recess 46, and the plunger 50 is in a position relative to the handle 20 in which the catches 54 are outside the handle 16; that is, the catches 54 are not received within the detents 26. However, the plunger 50 is so oriented with respect to the handle 16 that the catches 54 are aligned with the guide channels 28.

With the introducer in the ready condition, the cannula is positioned so that its tip is at or near the location of a tissue mass where a biopsy has been taken. Preferably, the cannula tip is positioned by using an imaging system. The cannula tip 38 can be designed for enhanced visibility using common imaging systems, such as CAT scan, ultrasonography and mammography. Suitable cannula tips are disclosed in U.S. Pat. No. 5,490,521, issued Feb. 13, 1996 to R. E. Davis and G. L. McLellan, which is incorporated by reference. Ultrasound enhancement technology is also disclosed in U.S. Pat. No. 4,401,124, issued Aug. 30, 1983 to J. F. Guess, D. R. Dietz, and C. F. Hottinger; and U.S. Pat. No. 4,582,061, issued Apr. 15, 1986 to F. J. Fry.

Once the cannula is positioned at the desired location, the plunger 50 is moved from its first or ready condition as illustrated in FIGS. 1 to 4 to a second or discharged condition as illustrated in FIG. 5 in which the catches 54 are received within the detents 26 to lock the plunger 50 in the discharged condition and the stylet shaft extends beyond the cannula tip 38. The catches 50 and detents combine to function as a latch for locking the plunger in the discharged condition. As the plunger 50 is moved from the ready condition to the discharged condition, the plunger 50 drives the stylet base 44 forward to advance the stylet shaft 42 within the cannula interior 36. As the stylet shaft 42 is advanced, the drug-eluting marker 60 is ejected from the marker recess 46 through the cannula tip 38 and into the tissue at the biopsy location.

The cannula 34 is illustrated with an opening formed in the cannula tip 38 communicating with the hollow interior 36; however the cannula 34 can optionally have an opening in a side wall of the cannula 34 that communicates with the hollow interior 36 and a closed tip 38, such that the drug-eluting marker 60 is ejected from the marker recess 46 through the side wall opening.

The drug-eluting tissue marker 60 is preferably readily imaged using contemporary imaging techniques. For example, the marker 60 can be made of material suitable to be imaged using X-ray, mammography, ultrasound, fluoroscopy, computed tomography, magnetic resonance imaging (MRI), computerized axial tomography (CAT) scan, Doppler, radiation detector, and any possible combination thereof. Optionally, the marker can be detectable by palpation of the overlying tissue or visualization of the marker using a colored material that is different that the surrounding tissue and blood. Regardless of the means, the marker 60 should be readily locatable within the tissue mass. Additionally, the marker 60 should not migrate within the tissue from the position in which it is initially placed. The marker 60 should be precisely and accurately locatable at the site, in case an additional medical procedure is needed. Returning to the biopsy example, if a tissue sample taken from a biopsy site is determined to be malignant or the pathology is inconclusive, an additional medical procedure at the site is necessary, in which case it is important to be able to locate the biopsy site.

The size and shape of the marker 60 can vary according to the application in which it is used. For example, lesions can have an effective size ranging from 2 mm to several centimeters, and thus the size and shape of the marker 60 can be configured according to the lesion size. As used herein, the term lesion has its normal meaning and expressly includes one or more micro-calcifications. The size of marker 60 has a practical upper limit that is related to the following factors. At some point the lesion will be large enough that it is palpable even after it is biopsied. For immediate relocating, such a lesion will not require the use of a marker as a surgeon or other practitioner will be able to find the lesion by palpitation. However, it still may be desirable to place a marker in anticipation of the lesion being reduced by future treatment, such as radiation. The marker should be large enough for easy location using the imaging system of choice, but should not be so big that it will obscure or interfere with imaging the lesion site. For these larger but not easily palpable lesions, a larger marker can be used without interfering with the imaging of the lesion site. For current imaging systems the useful upper size limit is about 10 mm for the maximum dimension, whereas the lower size limit is about 1 mm for the minimum dimension. By way of example, and without limitation, the marker 60 can have a length of about 3 mm and a width of about 1.5 mm.

FIGS. 6-9 illustrate four possible embodiments of the drug-eluting tissue marker 60; however, it is understood that the configuration of the marker 60 is not limiting to the invention and many other configurations of the marker 60 are possible without departing from the scope of the invention. For example, the marker 60 can have a hollow interior for enhanced imaging characteristics. Examples of other shapes are shown in U.S. Pat. Nos. 6,575,991; 6,371,904; 6,261,243; 6,228,055; and 6,056,700, all of which are incorporated herein by reference in their entirety.

A first embodiment of the marker 60 is shown in FIG. 6 having a bight portion 66 from which extend legs 67, which terminate in tips 68. The tips 68 extend in opposite directions to function as anchors for the marker 60 and help prevent the marker 60 from migrating from the site. The marker 60 further comprises a substrate 62 (partially shown) of underlying material that is coated with a drug 64. As used herein, the term "drug" can include any therapeutic agent, pharmacologic agent, or other substance used for the diagnosis, treatment, or prevention of a disease or as a component of a medication. A coating of the drug 64 can be deposited on the substrate surface using any suitable deposition technique. Alternately, the drug 64 can be embedded in a suitable material, such as a polymer, for timed release of the drug 64. At least a portion of the marker 60 is locatable from the exterior of the patient, through palpitation or through use of an imaging system.

The substrate 62 can be any number of materials that are suitably biocompatible and appropriate for the type of drug deposited on the substrate surface. The underlying material can be imageable to perform the marking function. Examples of materials for the substrate 62 include: stainless steel, tantalum, titanium, nitinol, gold, platinum, inconel, iridium, rhodium, silver, tungsten, or another biocompatible metal, or alloys of any of these; carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers thereof; polylactic acid, polyglycolic acid or copolymers thereof, a polyanhydride, polycaprolactone, polyhydroxy-butyrate valerate or another biodegradable polymer, or mixtures or copolymers of these; a protein, an extracellular matrix component, collagen, fibrin or another biologic agent; or a mixture thereof.

Some of these materials cannot be imaged using one of the aforementioned imaging techniques. In this case, an imageable material can be added to the drug coating 64 to enhance the radiopaque, mammographic, echogenic, etc. characteristics of the marker, allowing the marker to be observed with a corresponding imaging technique. For example, a contrast material such as iodine can be added to the coating to make the marker imageable during a CAT scan. Alternately, a separate coating can be deposited on the marker 60 in addition to the drug coating 64 to make the marker imageable.

Examples of the drug 64 include: anti-inflammatory, anti-platelet, anticoagulant, antifebrin, antithrombin, cytostatic, antiproliferative, antibiotic, antimicrobial, antioxidant, and antiallergic substances; antitumor and/or chemotherapeutic agents, including antineoplastic and antimitotic agents; thrombolytics; fibrinolytics, vasodilators; antiviral, antihypertensive, antisecretory, and immunosuppressive agents; growth factors and growth factor antagonists; antipolymerases; photodynamic therapy and antibody targeted therapy agents; prodrugs; sex hormones; free radical scavengers; radiotherapeutic, radiopaque, and radiolabelled agents; and peptides, proteins, and enzymes. Further, any combination of drugs, therapeutic agents, or other substances can be used to coat the marker of the present invention.

Examples of such anti-inflammatory substances include estradiol, aspirin, ibuprofen, and naproxen.

Examples of such antiplatelets, anticoagulants, antifibrin, and antithrombins include sodium heparin, low molecular weight heparins, heparinoids, hirudin, argatroban, forskolin, vapiprost, prostacyclin, prostacyclin analogues, dextran, D-phe-pro-arg-chloromethylketone (synthetic antithrombin), Dipyridamole, glycoprotein IIb/IIIa platelet membrane receptor antagonist antibody, recombinant hirudin, thrombin inhibitors such as Angiomax™ (Biogen, Inc., Cambridge, Mass.), glycoprotein IIbIIIa inhibitors, ticlopidine, clopidigrel, warfarin (e.g. Coumadin® from Bristol-Myers Squibb Co., Stamford, Conn.), aspirin, and hirulog.

Examples of such cytostatic or antiproliferative agents include, actinomycin D as well as derivatives and analogs thereof (manufactured by Sigma-Aldrich, Milwaukee, Wis.; or COSMEGEN® available from Merck & Co., Inc., Whitehouse Station, N.J.), angiopeptin, mitomycin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicines, fibroblast growth factor (FGF) antagonists, fish oil (omega 3-fatty acid), histamine antagonists, lovastatin (an inhibitor of HMB-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide.

Examples of such antiallergic substances include permirolast potassium, and tranilast.

Examples of such antitumor and/or chemotherapeutic agents include 2-chlorodeoxyadenosine (also known as cladribine), 6-thioguanine (also known as 2-amino-6-mercaptopurine), 13-cis-retinoic acid (also known as isoretinoin), aldesleukin (also known as interleukin-2), alemtuzumab, alitretinoin, all-trans retinoic acid (also known as tretinoin), alpha interferon, altretamine (also known as hexamethylmelamine), amifostine, aminoglutethimide, anagrelide, anastrozole, arsenic trioxide, asparaginase, azacitidine, azathioprine, BCG (*Bacillus Calmette-Guerin*), bevacizumab, bexarotene, bicalutamide, bleomycin, bortezomib, busulfan, capecitabine, carboplatin, carmustine, cetuximab, chlorambucil, cisplatin, cyclophosphamide, cytarabine (also known as arabinosylcytosine), cytarabine liposomal, dacarbazine, dactinomycin, daunorubicin liposomal, darbepoetin alfa, daunorubicin, decitabine, denileukin diftitox, dexamethasone (also known as dexamethasone sodium phosphate and dexamethasone acetate), dexrazoxane, docetaxel (e.g., Taxotere® from Aventis S.A., Frankfurt, Germany), doxorubicin, doxorubicin hydrochloride (e.g., Adriamycin® from Pharmacia & Upjohn, Peapack, N.J.), doxorubicin liposomal, epirubicin, epoetin alfa, estramustine, erlotinib, etoposide, exemestane, filgrastim, fluorouracil (also known as 5-fluorouracil), floxuridine, fludarabine, fluoxymesterone, flutamide, fulvestrant, gefitinib, gemcitabine, gemtuzumab, goserelin, ozogamicin, hydrocortisone (also known as cortisone), hydroxyurea, ibritumomab (also known as ibritumomab tiuxetan), idarubicin, ifosfamide, imatinib mesylate, irinotecan, lenalidomide, letrozole, leucovorin, leuprolide, lomustine, mechlorethamine (also known as nitrogen mustard, mustine, and mechlorethamine hydrochloride), megestrol (also known as megestrol acetate), melphalan, mercaptopurine (also known as 6-mercaptopurine), methotrexate (also known as amethopterin and methotrexate sodium), methylprednisolone, mesna, mitomycin (e.g., Mutamycin® from Bristol-Myers Squibb Co., Stamford, Conn.), mitoxantrone, nelarabine, nilutamide, octreotide (also known as octreotide acetate), oprevelkin, oxaliplatin, paclitaxel (e.g., TAXOL® by Bristol-Myers Squibb Co., Stamford, Conn.), paclitaxel protein-bound, pamidronate, peg interferon, pegaspargase, pegfilgrastim, pemetrexed, pentostatin, prednisolone, prednisone, procarbazine, raloxifene, rituximab, sargramostim, sorafenib, streptozocin, sunitinib, tamoxifen, temozolomide, teniposide, thalidomide, thiotepa (also known as thiophosphoamide), topotecan, toremifene, tositumomab (also known as iodine I-131), trastuzumab, vinblastine, vincristine, vinorelbine, and zoledronic acid.

Examples of such thrombolytics and/or fibrinolytics include tissue plasminogen activator (tPA), recombinant tPA, urokinase, streptokinase, tenecteplase, alteplase (e.g. Activase® from Genentech, Inc., San Francisco, Calif.), lysatec, antistreplase (e.g. Eminase® from Wulfing Pharma Gmbh, Germany), reteplase (e.g. Retavase® from Centocor, Inc., Malvern, Pa.), hannahpep (Indian King Cobra venom), ancrod (Malayan pit viper venom), and matrix metalloproteinases, such as collagenase.

Figure 7:
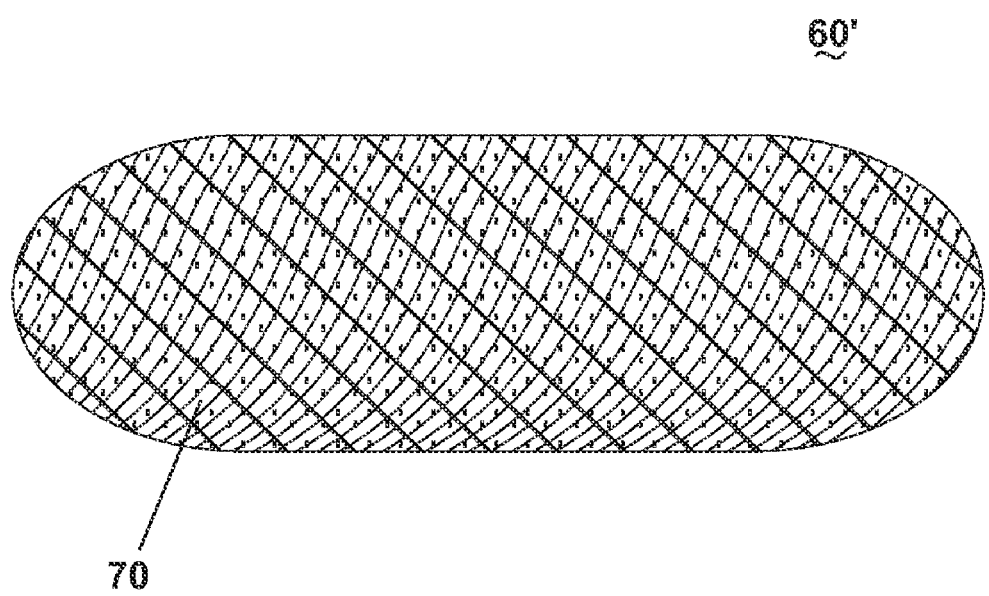
FIG. 7 is an enlarged view of a second embodiment of the drug-eluting marker according to the invention.

A second embodiment of the drug-eluting marker is shown in FIG. 7 in which like elements are designated with the same number bearing a prime (') symbol. The marker 60' can be comprised of a material 70 containing any of the drugs listed above. In this embodiment, the marker is made of a bioabsorbable material that will dissolve within the body at a predetermined rate, thus releasing the drug in a timed release fashion. Examples of such bioabsorbable materials are collagen, regenerated cellulose, synthetic polymers, and synthetic proteins.

Figure 8:
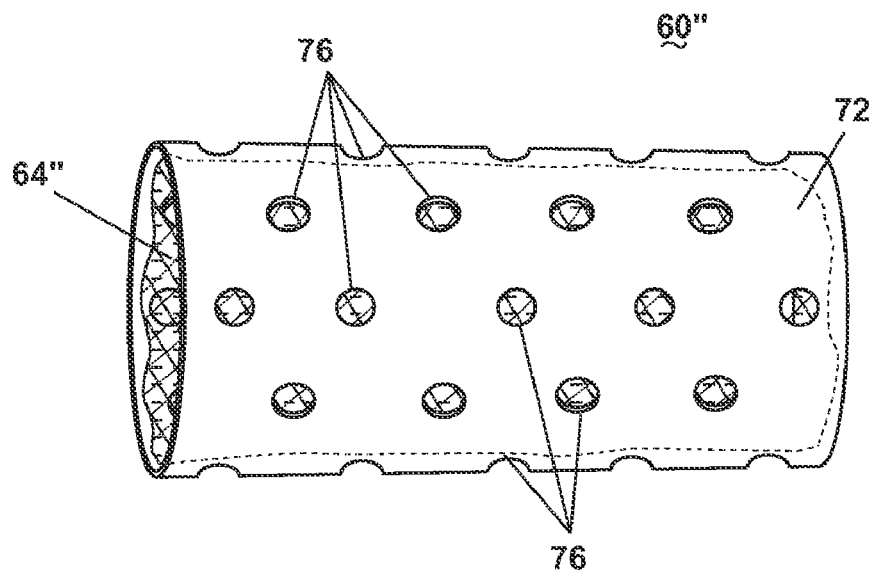
FIG. 8 is an enlarged view of a third embodiment of the drug-eluting marker according to the invention.

A third embodiment of the drug-eluting marker is shown in FIG. 8 in which like elements are designated with the same number bearing a double-prime (") symbol. The marker 60" encapsulates, either fully or partially, the drug 64". For illustrative purposes, the marker 60" is shown as a hollow tube 72, made of any of the materials listed above, that encapsulates the drug 64". Multiple pores 76 extend fully through the tube 72 to allow the drug 64" to pass through the exterior of the marker 60". The drug 64" can also pass through the open ends of the tube 72. The tube 72 can alternately be solid with pores 76, extending only partially through the tube, designed to hold the drug 64".

Figure 9:
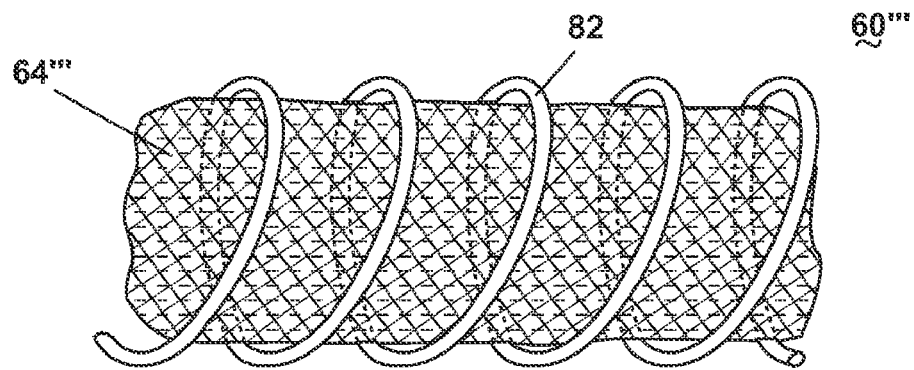
FIG. 9 is an enlarged view of an alternate design for the third embodiment of the drug-eluting marker according to the invention.

In an alternate design of the third embodiment shown in FIG. 9, where like elements are designated with the same number bearing a triple-prime ('") symbol, the marker 60'" can embody a spring-like configuration 82 that fully or partially encapsulates the drug 64'". The marker 60'" can further be made of a bioabsorbable material, as discussed above, that either fully or partially encapsulated the drug 64'".

As in the foregoing example, the marking apparatus 10 can be used to place a marker at the location of a tissue biopsy. However, the drug-eluting marker 60 can be used even if a biopsy has not been done. The drug-eluting marker 60 can be used as part of a treatment regimen whereby the drug 64 is delivered at a specific site within the body where the marker 60 is placed. For example, the marker 60 can be placed at a lesion detected using an imagining technique to mark the site prior to chemotherapy. The imageability of the marker 60 allows the lesion to be tracked during chemotherapy since the lesion often disappears during treatment. The drug-eluting capability of the marker 60 allows a suitable drug 64 to be delivered to the lesion as part of the treatment.

While the invention has been specifically described in connection with certain specific embodiments thereof, it is to be understood that this is by way of illustration and not of limitation, and the scope of the appended claims should be construed as broadly as the prior art will permit.

What is claimed is:

1. A tissue marker, comprising:
   a marker portion configured to mark a site within a soft tissue mass, the marker portion having a length extending along a centerline of the marker portion between a first end and a second end and having a substantially continuous wall along the length, the substantially continuous wall bounding a hollow interior; and
   a drug-eluting portion comprising a drug, wherein the drug-eluting portion is disposed within the hollow interior;
   wherein the length of the marker portion is greater than an average diameter of the hollow interior and wherein the substantially continuous wall includes at least one opening adapted to allow the drug to pass out of the hollow interior.

2. The tissue marker according to claim 1 wherein the marker portion has a maximum length of 10 mm.

3. The tissue marker according to claim 1 wherein the site comprises a lesion and the marker portion is configured to mark a lesion having an effective size of at least 2 mm.

4. The tissue marker according to claim 1 wherein at least one of the marker portion and the drug eluting portion is imageable.

5. The tissue marker according to claim 4 wherein the marker portion is imageable.

6. The tissue marker according to claim 1 wherein the marker portion comprises a structure that resists migration of the tissue marker from the site.

7. The tissue marker according to claim 6 wherein the structure includes an anchor.

8. The tissue marker according to claim 1 wherein the marker portion comprises a substrate and the drug-eluting portion comprises a coating on the substrate.

9. The tissue marker according to claim 1 wherein the drug-eluting portion is embedded in the marker portion.

10. The tissue marker according to claim 9 wherein the marker portion is bioabsorbable.

11. The tissue marker according to claim 10 wherein the marker portion is configured to dissolve within the soft tissue mass at a predetermined rate and release the drug in a timed release fashion.

12. The tissue marker according to claim 1 wherein the marker portion comprises a spring.

13. The tissue marker according to claim 1 wherein the at least one opening comprises a plurality of pores.

14. The tissue marker according to claim 1 wherein the site includes a lesion or a biopsy site.

15. The tissue marker according to claim 1 wherein the drug includes an anti-inflammatory, antiplatelet, anticoagulant, antifebrin, antithrombin, cytostatic, antiproliferative, antibiotic, antimicrobial, antioxidant, antiallergic, antitumor, chemotherapeutic, antineoplastic, antimitotic, thrombolytic, fibrinolytic, vasodilator, antiviral, antihypertensive, antisecretory, immunosuppressive, growth factor, growth factor antagonist; antipolymerase, photodynamic therapy, antibody targeted therapy, prodrug, sex hormone, free radical scavengers, radiotherapeutic, radiopaque, radiolabelled, peptides, proteins, and enzyme substance, or any combination thereof.

16. The imaging marker according to claim 1, wherein the marker portion is non-prosthetic.

17. An imaging marker comprising a marker portion and a drug-eluting portion comprising a drug, with the marker portion, the drug-eluting portion, or both, being imageable, the marker portion having a length extending along a centerline of the marker portion between a first end and a second end and having a substantially continuous wall along the length, the substantially continuous wall bounding a hollow interior and at least partially encapsulating the drug eluting portion within the hollow interior, and wherein the length of the marker portion is greater than an average diameter of the hollow interior and the substantially continuous wall includes at least one opening adapted to allow the drug to pass out of the hollow interior.

18. The imaging marker according to claim 17, wherein the marker portion comprises an imageable substrate and the drug-eluting portion comprises a coating containing the drug applied to the substrate.

19. The imaging marker according to claim 17, wherein the marker portion comprises a substrate of bioabsorbable material containing the drug.

20. The imaging marker according to claim 17, wherein the at least one of the marker portion and the drug-eluting portion is non-prosthetic.

21. A method for marking a site within a soft tissue mass, comprising:
    placing a marker into the soft tissue mass wherein the marker has a length extending along a centerline of the marker between a first end and a second end and has a substantially continuous wall along the length, the substantially continuous wall bounding a hollow interior and at least partially encapsulating a drug within the hollow interior, and wherein the length of the marker is greater than an average diameter of the hollow interior and the substantially continuous wall includes at least one opening adapted to allow the drug to pass out of the hollow interior; and
    eluting the drug from the marker.

22. The method according to claim 21 wherein the placing step comprises placing the marker at a lesion within the soft tissue mass.

23. The method according to claim 21 wherein the placing step comprises placing the marker at the site of a biopsy within the soft tissue mass.

24. The method according to claim 21 and further comprising locating the marker after the placing step.

25. The method according to claim 24 wherein the locating step comprises palpating the soft tissue mass or imaging the soft tissue mass.

26. The method according to claim 25 and further comprising conducting a medical procedure at the site after the locating step.

27. The method according to claim 26 and further comprising locating the site using an imaging system prior to the placing step.

28. The method according to claim 27 wherein the placing step comprises using an imaging system to embed the marker in a soft tissue mass.

29. A tissue marker, comprising:
    a marker portion configured to mark a site within a soft tissue mass, the marker portion being formed as a body having open ends, and having a substantially continuous wall bounding a hollow interior; and
    a drug-eluting portion comprising a drug, wherein the drug-eluting portion is disposed within the hollow interior of the body, and wherein the open ends facilitate a passing of the drug out of the hollow interior of the body to a region outside the body; and
    wherein the body is in the form of a tube having a plurality of openings that extend through the wall, and wherein the plurality of openings facilitate the passing of the drug out of the hollow interior of the tube to the region outside the tube.

* * * * *